(12) United States Patent
Ouwerkerk

(10) Patent No.: US 10,524,727 B2
(45) Date of Patent: Jan. 7, 2020

(54) CIRCADIAN PHASE DETECTION SYSTEM

(71) Applicant: KONINKLIJKE PHILIPS N.V., Eindhoven (NL)

(72) Inventor: Martin Ouwerkerk, Culemborg (NL)

(73) Assignee: Koninklijke Philips N.V., Eindhoven (NL)

( * ) Notice: Subject to any disclaimer, the term of this patent is extended or adjusted under 35 U.S.C. 154(b) by 204 days.

(21) Appl. No.: 15/314,202

(22) PCT Filed: Jun. 8, 2015

(86) PCT No.: PCT/EP2015/062630
§ 371 (c)(1),
(2) Date: Nov. 28, 2016

(87) PCT Pub. No.: WO2015/189107
PCT Pub. Date: Dec. 17, 2015

(65) Prior Publication Data
US 2017/0196510 A1 Jul. 13, 2017

(30) Foreign Application Priority Data
Jun. 12, 2014 (EP) .................................... 14172102

(51) Int. Cl.
*A61B 5/00* (2006.01)
*A61B 5/053* (2006.01)
*A61B 5/01* (2006.01)

(52) U.S. Cl.
CPC .............. *A61B 5/4857* (2013.01); *A61B 5/01* (2013.01); *A61B 5/0533* (2013.01);
(Continued)

(58) Field of Classification Search
CPC ..... A61B 5/4806–4821; A61B 5/4857; A61M 2021/0083
See application file for complete search history.

(56) References Cited

U.S. PATENT DOCUMENTS

2006/0142968 A1  6/2006 Han et al.
2006/0293602 A1* 12/2006 Clark .................... A61M 21/00
                                                                 600/500
(Continued)

FOREIGN PATENT DOCUMENTS

DE       4221526 A1    1/1994
EP       1982747 A1   10/2008
JP      04367653 A  * 12/1992
WO  WO 2012140537 A1 * 10/2012 ........... A61B 5/0533
WO       2013011416 A1    1/2013

OTHER PUBLICATIONS

Machine translation of JP 04367653 A.*
(Continued)

*Primary Examiner* — David J. McCrosky

(57) ABSTRACT

The present invention relates to a device (10) for detecting a circadian phase shift of a user (48). The device comprises: an interface for obtaining a skin conductance signal of the user (48) and sleep cycle information of the user (48); a processing unit (14) for determining an internal clock wake-up time based on the obtained skin conductance signal (20) and an external clock wake-up time based on the obtained sleep cycle information; and an evaluation unit (16) for evaluating a circadian phase shift of the user (48) based on the internal clock wake-up time and the external clock wake-up time. The present invention further relates to a corresponding method as well as to a wearable system (22) for monitoring a circadian phase shift of a user (48).

10 Claims, 4 Drawing Sheets

(52) U.S. Cl.
CPC .......... *A61B 5/4809* (2013.01); *A61B 5/4812* (2013.01); *A61B 5/681* (2013.01); *A61B 2560/0247* (2013.01); *A61B 2562/0219* (2013.01)

(56) References Cited

U.S. PATENT DOCUMENTS

| | | | |
|---|---|---|---|
| 2009/0105560 | A1 | 4/2009 | Solomon |
| 2010/0041965 | A1 | 2/2010 | Kang et al. |
| 2010/0041966 | A1 | 2/2010 | Kang et al. |
| 2010/0268056 | A1 | 10/2010 | Picard et al. |
| 2011/0288607 | A1 | 11/2011 | Cholette |
| 2012/0142999 | A1 | 6/2012 | Albu et al. |
| 2013/0002435 | A1* | 1/2013 | Utter, II ............... A61B 5/0022 340/575 |
| 2013/0338470 | A1 | 12/2013 | Ouwerkerk |
| 2014/0031704 | A1 | 1/2014 | De Vries et al. |

OTHER PUBLICATIONS

Kobayashi, Rei, et al. "Skin sympathetic nerve function during sleep—a study with effector responses." Autonomic Neuroscience 103.1-2 (2003): 121-126. (Year: 2003).*

Johns, M. W., B. A. Cornell, and J. P. Masterton. "Monitoring sleep of hospital patients by measurement of electrical resistance of skin." Journal of applied physiology 27.6 (1969): 898-901. (Year: 1969).*

Serkh, Kirill, and Daniel B. Forger. "Optimal schedules of light exposure for rapidly correcting circadian misalignment." PLoS computational biology 10.4 (Apr. 10, 2014): e1003523. (Year: 2014).*

Till Roenneberg et al: "Social Jetlag and Obesity", Current Biology, Current Science, GB, vol. 22, No. 10, Mar. 20, 2012 (Mar. 20, 2012), pp. 939-943.

Till Roenneberg et al: "Supplemental Information Social Jetlag and Obesity", Current Biology, Mar. 20, 2012 (Mar. 20, 2012).

Panza et al, "Circadian Variation in Vascular Tone and Its Relation to α-Sympathetic Vasoconstrictor Activity", The New England Journal of Medicine, 1991, pp. 986-990.

Roenneberg, "Chronogiology: The Human Sleep Project", Nature, vol. 498, 2013, pp. 427-428.

Wüst et al, "Genetic Factors, Perceived Chronic Stress, and the Free Cortisol Response to Awakening", Psychoneuroendocrinology 25. 2000, pp. 707-720.

Fries et al, "The Cortisol Awakening Response (CAR): Facts and Future Directions", International Journal of Psychophysiology, vol. 72, 2009, pp. 67-73.

* cited by examiner

CIRCADIAN PHASE DETECTION SYSTEM

CROSS-REFERENCE TO PRIOR APPLICATIONS

This application is the U.S. National Phase application under 35 U.S.C. § 371 of International Application No. PCT/EP2015/062630, filed on Jun. 8, 2015, which claims the benefit of European Patent Application No. 14172102.7, filed on Jun. 12, 2014. These applications are hereby incorporated by reference herein.

FIELD OF THE INVENTION

The present invention relates to a system and method for monitoring a circadian phase shift of a user.

BACKGROUND OF THE INVENTION

Within each day exists a cycle that affects attention, alertness, energy and mood of a human being. This internal rhythm is produced and regulated by a neurological mechanism called the circadian clock. In healthy humans, the secretion of cortisol from the adrenal glands follows a diurnal cycle with a profound increase after awakening. This increase after awakening, a phenomenon termed the cortisol awakening response, appears to be a distinct feature of the hypothalamus-pituitary-adrenal axis, superimposing the circadian rhythmicity of cortisol secretion. Another circadian effect is the morning surge of blood pressure. A sudden activation of the sympathetic nervous system is the primary mediator of the morning surge. Increased-mediated sympathetic vasoconstriction has been found in normal subjects. Whereas arousal from sleep is associated with a slight rise in plasma epinephrine, arising induces a significant rise both in epinephrine and norepinephrine.

In Panza et al., "Circadian variation in vascular tone and its relation to α-sympathetic vasoconstrictor activity", N Engl J Med 1991; 325:986-990, it is described that there is a circadian rhythm in basal vascular tone, due either partly or entirely to increased alpha-sympathetic vasoconstrictor activity during the morning. This variation may contribute to higher blood pressure and the increased incidence of cardiovascular events at this time of day.

Current methods for circadian phase detection usually require obtrusive sampling methods. One the one hand, it is possible to derive information on the circadian phase from the core body temperature. The core body temperature can be measured with an intra body sensor, such as an e-pill. Having to swallow an e-pill and to retrieve it from excrements is cumbersome. Alternatively, the temperature in the mouth or in the armpit can be measured, which may also be inconvenient to the individual. On the other hand, it is possible to derive information on the circadian phase from a salivary melatonin test. The salivary testing of melatonin requires the regular sampling of saliva. This is a burden to the individual.

In DE 4221526 A1 a system for controlling, measuring and training psycho-emotional adaption processes is disclosed. The system serves for non-invasively verifying different psycho-emotional states like arousal, stress, fear, relaxation, impact of ataractics etc. The system evaluates the secretion of the perspiratory glands by means of pulsating direct current. The system is implemented in the form of a wristwatch and converts electric values of the skin conductance into analog angle readings. A high arousal (low skin conductance) corresponds to a high angle reading (high impulse frequency).

In Till Roenneberg: "Chronobiology: The human sleep project", Nature, June 2013, a research activity at the University of Munich is presented. Researchers have gathered a database including entries for more than 150.000 individuals from all over the world that have provided the times at which they go to bed, prepare for sleep, fall asleep, wake-up and get up.

Consequently, it is desirable to provide an approach for unobtrusive circadian phase detection. Such an approach could be used to provide a gentle adaption of the circadian phase of a person to an external requirement.

SUMMARY OF THE INVENTION

It is an object of the present invention to provide a device that allows unobtrusively detecting a circadian phase shift of a person. It is further an object of the present invention to provide a wearable system for monitoring a circadian phase shift of a person.

In a first aspect of the present invention a device for detecting a circadian phase shift of a user is presented. The device comprises:

an interface for obtaining a skin conductance signal of the user and sleep cycle information of the user;

a processing unit for determining an internal clock wake-up time based on the obtained skin conductance signal and an external clock wake-up time based on the obtained sleep cycle information; and an evaluation unit for evaluating a circadian phase shift of the user based on the internal clock wake-up time and the external clock wake-up time.

In a further aspect of the present invention a method for detecting a circadian phase shift of a user is presented. This method comprises the steps of:

obtaining a skin conductance signal of the user and sleep cycle information of the user;

determining an internal clock wake-up time based on the obtained skin conductance signal and an external clock wake-up time based on the obtained sleep cycle information; and evaluating a circadian phase shift of the user based on the internal clock wake-up time and the external clock wake-up time.

In yet another aspect of the present invention a wearable system for monitoring a circadian phase shift of a user is presented. The wearable system comprises a device as defined above and a skin conductance sensor unit.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

Mood problems, sleep disorders, seasonal affective disorder, depression, can often be traced to a circadian clock problem. This is of particular relevance for persons travelling through time zones and having to adapt their circadian rhythm to external requirements (e.g. meeting in the morning after a flight into another time zone). Possible approaches to alleviate negative effects of a circadian phase being out of sync with an external clock include the use of devices that allow providing a gentle circadian phase shift by means of an adaption of light or sound etc. to the circadian phase of a person. Such devices include the Philips Wakeup light, the Philips Golite blue, or the Philips Britelite SAD lamp. If, however, it is desired that a device reacts to the current circadian phase of a person, a simple, fast and unobtrusive measurement of the circadian phase is needed.

The present invention is based on the idea of unobtrusively determining the circadian phase shift of a person or user from a skin conductance measurement of the user. Based on an evaluation of the obtained skin conductance signal or measurement of the skin conductance, an internal clock wake-up time is determined. This internal clock wake-up time corresponds to the time the circadian clock of the user indicates that the user is waking up, i.e. to his circadian rhythm. This internal clock wake-up time is compared to an external clock wake-up time which indicates the actual time the user gets up (or desires to get up). This external clock wake-up time is determined based on obtained sleep cycle information of the user. The external clock wake-up time may, e.g., correspond to the time of an alarm clock, the break of dawn or a time of increased noise in the ambience of the user. Particularly, the external clock wake-up time may correspond to the time the user wakes up or at least should wake up considering the local time at his location. Based on the comparison of the internal clock wake-up time and the external clock wake-up time, the circadian phase shift of the user can be evaluated. This circadian phase shift of the user indicates whether or not the user (i.e. the user's circadian phase) is in time or synchronized with the external rhythm or external time at his current location.

In comparison to previous approaches for determining a circadian phase shift of a user which, as outlined above, usually required obtrusive sampling methods and a higher effort of the user, the present invention provides a simple, inexpensive and easy-to-use approach for deriving information on a circadian phase shift. Such information can, e.g., be used for controlling a circadian phase shift device. If it is determined that a user's circadian clock is not in sync with the external clock, i.e. that the user is subject to a circadian phase shift, such a device may help the user to recover his natural rhythm. A device as described above may, e.g., be used for shift workers, long distance travelers or persons working underground that have to adapt their rhythm frequently and that are subject to time shifts. Other application areas may be in the field of patients or medical personnel in intensive care units In a preferred embodiment the processing unit is configured to determine a rise time of a skin conductance response based on the skin conductance signal; and determine a time period of decreased rise times of the skin conductance response indicating the internal clock wake-up time.

One approach for deriving the internal clock wake-up time from the skin conductance signal is to evaluate a rise time of a skin conductance response. The (usually time-based) skin conductance signal exhibits peaks that are referred to as skin conductance responses. To extract a skin conductance response (or a plurality of skin conductance responses) from the skin conductance signal, these peaks are identified. Then, a rise time of the skin conductance response is determined, whereby a rise time of a skin conductance response refers to the time it takes for the skin conductance signal to reach a maximum point (a peak in the skin conductance signal). Thus, the skin conductance signal is processed to identify skin conductance responses and to determine the rise time of the skin conductance responses. This time is referred to as the rise time of the skin conductance response.

Based on this rise time of the skin conductance response, it is possible to determine the internal clock wake-up time. It has been observed that this rise time is decreased in a time period following the internal clock wake-up time as defined by the circadian rhythm of the user. Thus, the rise time or, more precisely, the monitoring of the rise time over a time period, allows identifying the time the user wakes up according to his circadian rhythm. Consequently, a simple signal processing of the skin conductance response is sufficient for determining the internal clock wake-up time.

In a preferable embodiment the processing unit is configured to determine the time period of decreased rise times of the skin conductance response by monitoring an average of the rise times of the skin conductance response.

The rise times of the skin conductance responses vary. Thus, to reliably determine a time period of decreased rise times that indicates the internal clock wake-up time, it may be advantageous to monitor an average (e.g. a moving average) of the rise times. Based on this average, it becomes possible to determine the internal clock wake-up time by, e.g., applying a threshold. As soon as the average of the rise times of the skin conductance response falls below a predefined threshold, it is detected that the user wakes up.

On the one hand, it is possible to retrospectively identify the time period of decreased rise time by evaluating the average of the rise time of the skin conductance response during a time period (e.g. one day). For this, it is sufficient to identify a time period of decreased average of the rise times, i.e. a time period during which the rise times are (significantly, e.g. 15% to 30% on a relative scale) lower than during the remaining time in which the average of the rise times has been monitored. On the other hand, e.g. if a continuous monitoring of the circadian rhythm is desired, it is also possible to monitor a moving average or another figure indicating the development of the rise times of the skin conductance response over time and determine, e.g. based on thresholding (when the monitored average falls below a predefined threshold), that a significant reduction of the average rise time occurs. This allows providing a real-time monitoring and identification of the internal clock wake-up time.

In yet another embodiment the evaluation unit is configured to compare the external clock wake-up time with the internal clock wake-up time to determine a time difference indicating the circadian phase shift. A simple approach for determining information on the circadian phase shift of a user includes comparing the external clock wake-up time with the internal clock wake-up time. Both the external and the internal clock wake-up time may refer to a point in time or to a time period (e.g. the half hour after waking up). For points in time a difference may be determined. This is also possible in the case of time periods, e.g. by subtracting the beginning or end times. Based on this difference it can be determined whether the circadian rhythm of the user is in sync with an externally induced time regime. If the internal clock wake-up time is significantly after the external clock wake-up time, this may indicate that the user is not in sync with the external time at his location. Such a situation may result in a higher level of stress and/or a lower robustness against influences from the environment of the user. This may occur, e.g., for travelers that frequently travel from one time zone to another. Thereby, it is advantageous that no complicated signal processing is required to derive a meaningful parameter that indicates whether or not the circadian rhythm of a person corresponds with the external rhythm as induced by the environment (other persons, specific location, etc.).

In yet another embodiment the sleep cycle information includes at least one of acceleration sensor information indicative of a movement of a body part of the user;

light sensor information indicative of an ambient light level in an ambience of the user; and skin temperature information indicative of a skin temperature of the user.

The external clock wake-up time may particularly be derived from a sensor, e.g. an acceleration sensor, a light sensor or skin temperature sensor. Usually, the sensor information will be interpreted in the light of the local time. The sensors rely on different approaches for determining the external clock wake-up time. An acceleration sensor that is applied to a body part of the user allows evaluating an acceleration that occurs when user gets up. The wake-up time may be identified based on an evaluation (pattern recognition, thresholding, etc.) of an acceleration signal. The user getting up indicates that the user's external wake-up time has come. A light sensor may measure the illumination of an ambience of the user. Usually, a user will switch on the light as soon as he gets up or the illumination will increase at the moment of dawn at the location of the user. Thus, also a light sensor may provide information that indicates the time a user gets up or should get up (i.e. the external wake-up time). The information of the light sensor is independent of the time zone or location of the user, which is particularly advantageous for (frequent) travelers. Still further, the skin temperature of a user may show a characteristic behavior at the time a user wakes up or in period following the time the user wakes up. For instance, this effect may be caused by the user being covered with a blanket during the time he is in his bed and having an increased skin temperature caused by this blanket. Thus, the sleep cycle information may include different types of information that can all be individually or in a combination used to determine the time a user gets up. If his internal wake-up time has not yet come this indicates that he is subject to a circadian phase shift. Depending on the individual user, it may make sense to combine different of the above-described information sources to reliably determine the time the user gets up.

In yet another embodiment the device further comprises a control unit for determining control parameters to control a circadian phase shift device based on the circadian phase shift of the user. Such a circadian phase shift device allows providing an external stimulus to a user which helps to gently adapt the circadian rhythm to external requirements. Thus, the control unit has the advantage that it becomes possible to exploit the information provided by the device of the present invention in to overcome the negative effects of a circadian rhythm of a user being out of sync with an external time as induced by the environment of the user. Such a circadian phase shift device may be used by shift workers or long distance travelers or persons with sleep disorders.

In a preferable embodiment of the wearable system of the present invention there is further comprised a wristband for supporting the system at a limb of the user. The system thus corresponds to a type of device that can be attached to a limb such as an arm, leg, finger, etc. of a user. This implementation of the system may, e.g., take the form of a wristwatch or the like. It is particularly advantageous if the system of the present invention affects the behavior of the user as little as possible. One approach that results in a very small or inexistent interference with the normal behavior of the user is to implement the system in the form of a device that includes a wrist band. This may allow the user to wear the system and to not need to individually perform a measurement act or the like whenever he desires to make use of the system of the present invention.

In a preferable embodiment the skin conductance sensor unit includes two electrodes for measuring a conductance when being applied to a skin portion of the user. Usually, a testing current is applied to the skin of the user in order to derive information on the skin conductance or skin conductance response of the user. The electrodes require direct contact with the skin of the user. It may be advantageous to provide the electrodes at a position of the wrist band that allows comfortably wearing the system with the electrodes in contact with a body part, such as an ankle, the palm of a hand, a sole, the wrist of the person.

In yet another preferable embodiment the system further comprises a sleep cycle unit including at least one of an acceleration sensor for obtaining acceleration sensor information indicative of a movement of a body part of the user;

a light sensor for obtaining light sensor information indicative of an ambient light level in an ambience of the user; and a temperature sensor for obtaining skin temperature information indicative of a skin temperature of the user.

As outlined above, the sleep cycle information may particularly include acceleration sensor information, light sensor information or temperature sensor information. This information may be obtained by different sensors included in a system as defined above. One advantage of integrating the required sensor or sensors into the device of the present invention is that no external devices are needed. Thereby, an efficient implementation the system becomes possible. Also, integrating the required sensor or sensors into the system itself allows avoiding compatibility issues or issues with respect to transmission errors between the sensor and the system. If all sensors along with the necessary signal processing equipment are integrated into the same system, no data transmission is required.

Preferably, the system may further comprise an output interface for providing information on the circadian phase shift of the user. This output interface may thus allow communicating with the user and forward the determined information to the user. Then, a user can decide whether or not steps need to be taken to realign the circadian rhythm with the externally induced rhythm. Furthermore, the user may obtain an explanation of an eventual problem caused by a lack of synchronization between his circadian rhythm and an externally induced rhythm.

Further preferably, the system further comprises an input user interface for obtaining sleep cycle information from the user. This input user interface allows the user to provide information that can be evaluated in order to determine the external clock wake-up time. Such information may include the time the user sets his alarm clock or the time of a meeting etc.

Still further, the system may comprise a communication interface for communicating with a circadian phase shift device. Such a communication interface may allow controlling, i.e. directly communicating with a circadian phase shift device and transmit the determined data or the required control parameters. This is particularly of interest if the system of the present invention is used for determining control parameters for controlling a circadian phase shift device.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
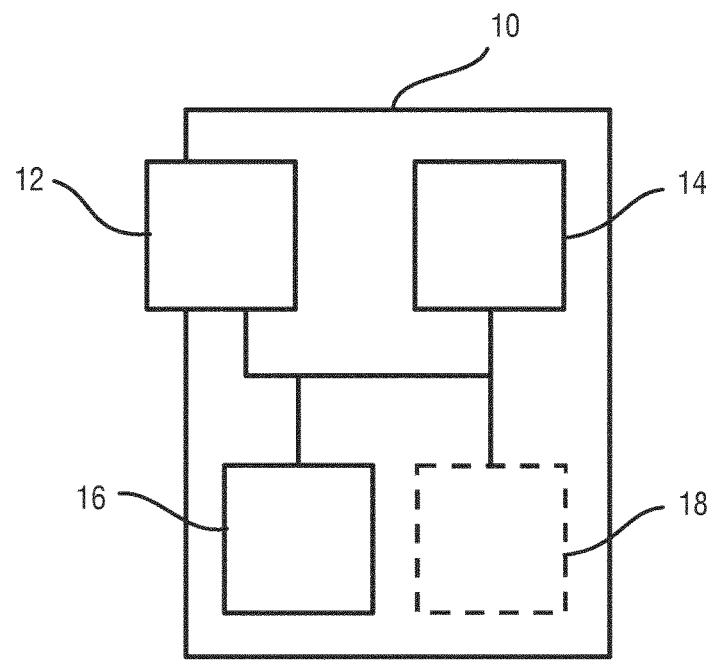
FIG. 1 shows a schematic illustration of a device for detecting a circadian phase shift of a user according to an aspect of the present invention.

FIG. 1 shows a schematic illustration of a device 10 for detecting a circadian phase shift of a user according to a first aspect of the present invention. The device 10 comprises an interface 12 for obtaining a skin conductance signal of the user and sleep cycle information of the user. Further, the device comprises a processing unit 14 and an evaluation unit 16. Optionally, the device 10 may further comprise a control unit 18 which is illustrated in FIG. 1 by a dashed line to illustrate that it may or may not be comprised in some embodiments of the present invention.

The basic idea of the present invention is to provide an unobtrusive approach for determining the circadian phase or circadian clock of a human or mammal and deriving therefrom whether this circadian clock is in sync with an external clock or external rhythm (circadian phase shift). The device 10 obtains a skin conductance signal and derives therefrom an internal clock wake-up time. This internal clock wake-up time may correspond to a time period, e.g. a time period of 30 minutes or the like, that indicates the time interval in which the user gets up or, more precisely, the time interval the circadian clock of the user indicates that he wakes up. The internal clock wake-up time may also correspond to a precise time specification carrying corresponding information. Usually, however, the internal clock wake-up time refers to a time interval of 30 minutes. As used herein, the skin conductance signal refers to a signal indicating the skin conductance (usually indicated on a Siemens scale to describe the electric conductance). Such a time-based skin conductance signal is processed and analyzed and signal parameters are derived therefrom as further detailed below. Based on the evaluation of the signal information the internal clock wake-up time is derived. This internal clock corresponds to the time of the cortisol awakening response or to the blood pressure morning surge.

In addition to the internal clock wake-up time an external clock wake-up time is determined based on sleep cycle information of the user. As used herein, the external clock wake-up time may particularly refer to a time interval or an exact time that indicates when a user gets up. In some embodiments, the external clock wake up time may also describe the time a day starts at the current location of a user (e.g. in the case of a long distance traveler that suffers from a time-shift).

The internal clock wake-up time and the external clock wake-up time are usually indicated on the same scale. The external clock wake-up time is determined based on sleep cycle information. Such sleep cycle information may be provided by the user himself via a user interface or may also be obtained from a sensor unit by means of which a physical phenomenon can be converted to an electronic signal which is related to the external clock wake-up time.

As used herein, an external time refers to an induced time in contrast to the internal time of a user, which refers to the circadian phase of the user. An external time may particularly refer to a local time at the location of the user. Usually, the circadian phase or circadian clock of the user should be synchronized with the local time or external time. Thus, the time the user wakes up or should wake up at his present location (external clock wake-up time of the user) should correspond to his internal wake-up time. Herein, synchronized indicates that the circadian clock and the external time (actual time) are in phase.

This synchronization may, however, be disturbed by a time shift after a long distance flight over multiple time zones or if an external rhythm is induced that does not correspond to the circadian phase in case of nightshift workers or the like. Also people suffering from sleep disorders have problems with aligning their circadian clock to the external time. Then, the circadian phase and the external time are not synchronous anymore. The present invention aims at providing a device that allows detecting this situation, i.e. a circadian phase shift of a user. As used herein, a user refers to a living being, in particular a human being.

One or more of the interface 12, processing unit 14, evaluation unit 16 and control unit 18 of the present invention may partly or entirely be implemented in the form of one or more microprocessors (MCU, FPGA, ASIC, etc.). The described functionalities may partly or entirely be implemented in hard- and/or software.

Embodiments of the present invention may include body worn devices, such as devices for personal health monitoring or the like, smartphone apps that rely on input data provided by external sensors or by the user himself, Internet- or server-based implementations in which the required skin conductance response of the user and sleep cycle information of the user are provided by the user or an adequate sensor unit via Internet or network communication, etc. All different implementations of a device according to the illustrated embodiment of the present invention rely on the basic idea of determining an internal clock wake-up time based on a skin conductance response of a user and an external clock wake-up time based on sleep cycle information of the user and derive therefrom a circadian phase shift of the user.

Depending on the embodiment, the determined information on the circadian phase shift of the user may either be provided to the user so that the user can react by changing his behavior or that the user can at least be supplied with an explanation of his current feeling or the like. Alternatively the information may be provided to a device or to medical support personnel such as a physician.

Figure 2:
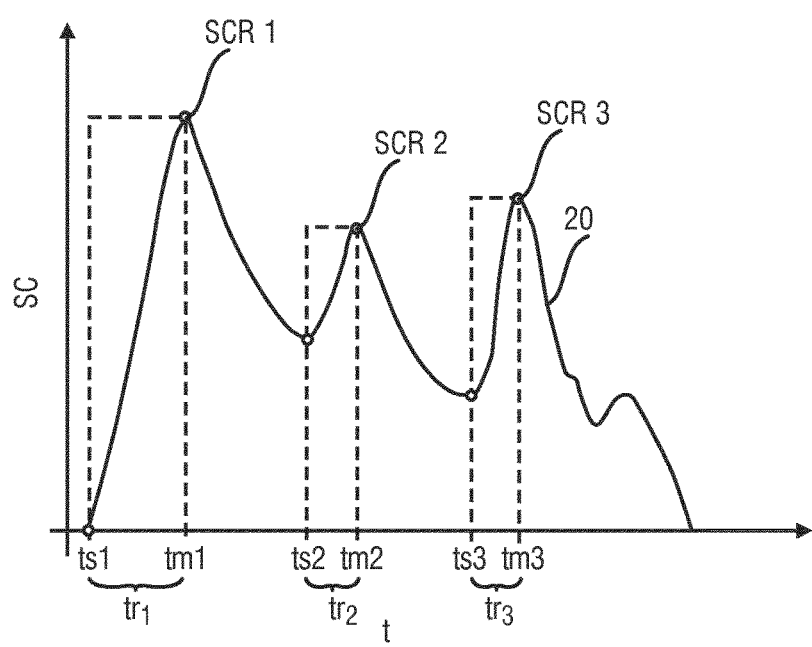
FIG. 2 illustrates the signal processing of a skin conductance signal of a user as used in an embodiment of the present invention.

In FIG. 2 an example of a skin conductance (SC) signal is illustrated to illustrate a possible data processing approach according to the present invention. The illustrated skin conductance signal 20 exhibits peaks, which are referred to as skin conductance responses SCR1, SCR2 and SCR3. These skin conductance responses SCR1, SCR2 and SCR3 may be identified from the skin conductance signal by means of peak detection algorithms and may also be subject to further conditions, such as thresholds or minimum height or duration specifications etc. For instance, the skin conductance responses may be detected by evaluating the slope or gradient of incline at subsequent points of the skin conductance signal. If the slope exceeds a given value, it may be determined that a skin conductance response SCR is present. Then, a point in time ts1, ts2, ts3 may be identified that indicates where the SCR starts. Furthermore, a maximum time point tm1, tm2, tm3 that indicates where the SCR is at its maximum can be identified. Based on these considerations, a rise time tr1, tr2, tr3 can be determined for each SCR by subjecting the onset time point from the maximum time point for each SCR. Thus, for each skin conductance response SCR1, SCR2, SCR3 a value of the rise time of this skin conductance response tr1, tr2, tr3 can be exactly determined.

In previous approaches, it has been demonstrated that this rise time of the SCR correlates with the systolic blood pressure of an individual. The blood pressure of healthy individuals not suffering from chronic high blood pressure shows a marked increase in the early morning hours after getting up. This increase may typically be between 15 and 20 mmHg, on an average value of 120 mmHg. It has been shown that the rise times of the skin conductance responses shorten when the blood pressure increases. When the average rise time of the skin conductance responses of 48 consecutive 30-minute periods are listed in a 24-hour graph, the blood pressure morning surge stands out as a dip/valley. The minimum indicates the period centered 30 minutes after wake-up. This is coincident with the maximum of the cortisol awakening response as has been shown in Fries et al., "The Cortisol Awakening Response (CAR): Facts and Future Directions", International Journal of Psychophysiology, 2009. The present invention exploits this connection of the skin conductance response in particular with respect to the rise times of the skin conductance response with the circadian phase of the person. It is exploited that the rise times of the skin conductance response are shorter in the 30-minute interval after a user wakes up (corresponding to his internal wake-up time). Thereby, it is advantageous if the duration of the time period of decreased average of the rise times corresponds to the duration of the cortisol awakening peak width (cf. Wüst et al., "Genetic factors, perceived chronic stress, and the free cortisol response to awakening", Psychoneuroendocrinology 25 (2000) 707-720).

Both the blood pressure rise and the decrease of the rise time of the skin conductance response may result from the same origin, i.e. the cortisol awakening response. Usually, the SCR rise times vary from 1 to 2.5 seconds. This corresponds to approximately 180 mm Hg systolic and approximately 100 mm Hg systolic blood pressure respectively. The morning surge is about 15-20 mm Hg. Thus, the rise times will be decreased by about 18.75 to 25%.

As described before, arousal from sleep is associated with a slight rise in plasma epinephrine, arising induces a significant rise both in epinephrine and norepinephrine. The skin conductance level seems to be linked to norepinephrine. It is one of the two transmitter chemicals of the sympathetic nerve. The other, acetylcholine is responsible for skin conductance responses, which are short lived (10 seconds max.).

In preferable embodiments of the present invention this detection of decreased rise times of the skin conductance response may be based on a retrospective analysis of the recorded skin conductance signal and the skin conductance responses during a time period, such as a day. Then, the internal clock wake-up time can be easily identified by comparing the development of an average value of the skin conductance response rise times over time. When this average value exhibits a minimum, this minimum indicates that the user is waking up (according to his internal clock or circadian phase).

According to the present invention the determined internal clock wake-up time is then compared to an external clock wake-up time that is derived from sleep cycle information of the user.

It is to be understood that FIG. 2 shows a schematic example of the processing according to the present invention. The illustrated three peaks (SCR1, SCR2 and SCR3) are intended to schematically illustrate the data processing. Usually, a number of SCR's are evaluated by means of an average.

Figure 3:
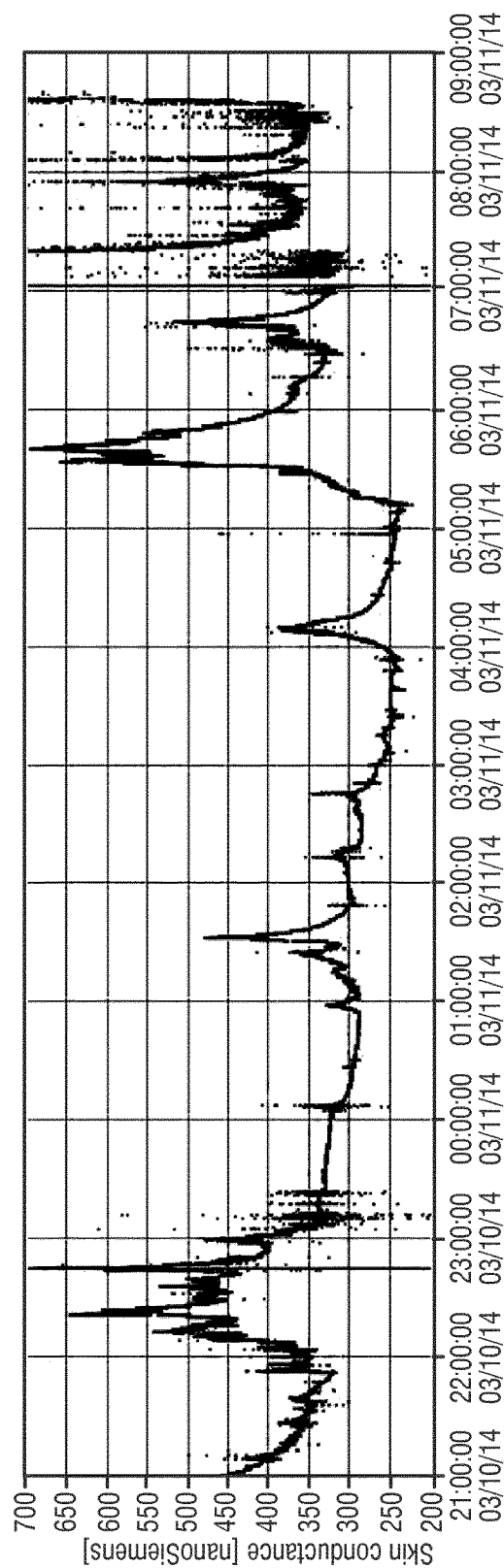
FIG. 3 shows an example of an actual measurement of a skin conductance signal of a user.

FIG. 3 illustrates an actual measurement at 142 systolic BP. The measurement is elevated and thus representative of how it would look at the peak of the cortisol awakening response for a healthy person with normal blood pressure. Usually, all SCR's in an epoch of about 20 or 30 minutes will be evaluated and an average will be calculated to increase sensitivity.

Figure 4:
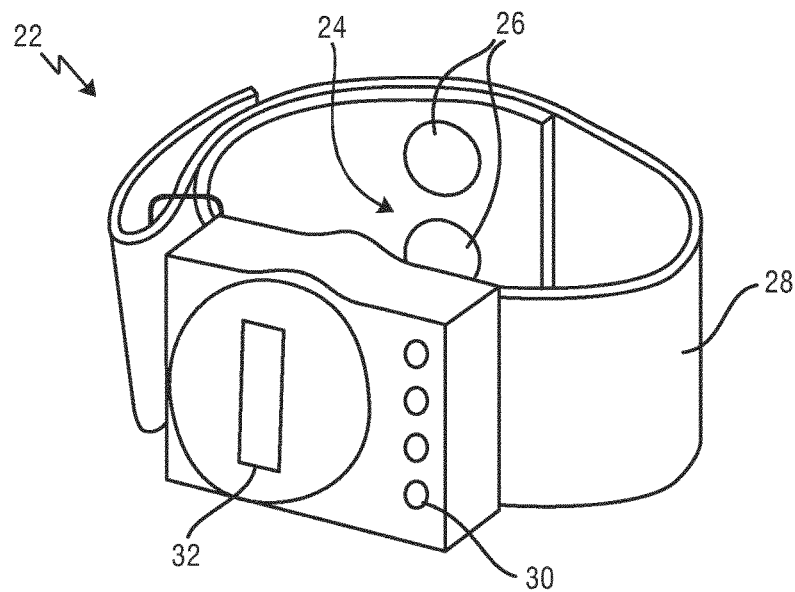
FIG. 4 illustrates an embodiment of a wearable system according to an aspect of the present invention in the form of a wristwatch.

The device 10 of the present invention may particularly be included in a wearable system 22 as illustrated in FIG. 4. As illustrated, this wearable system 22 may particularly be in the form of a wristwatch, such as the Philips discrete tension indicator DTI-2. Apart from the device 10 as described above, the system 22 also includes a skin conductance sensor unit 24 for measuring the skin conductance of a person wearing the system 22 attached to his wrist. In other embodiments of the present invention, it may also be possible that a system according to an aspect of the present invention is worn at the ankle or at a finger or at other body parts of a user.

In particular, the skin conductance sensor unit includes two electrodes 26 which can be used for measuring an electrical resistance or a conductance when being applied to a skin portion of the user.

The system 22 is usually supported at a limb of the user by means of a wrist band 28 and has control elements 30 (corresponding to a user input interface) as well as feedback elements 32 (corresponding to a user output interface) for allowing a user to provide information and to obtain information.

Figure 5:
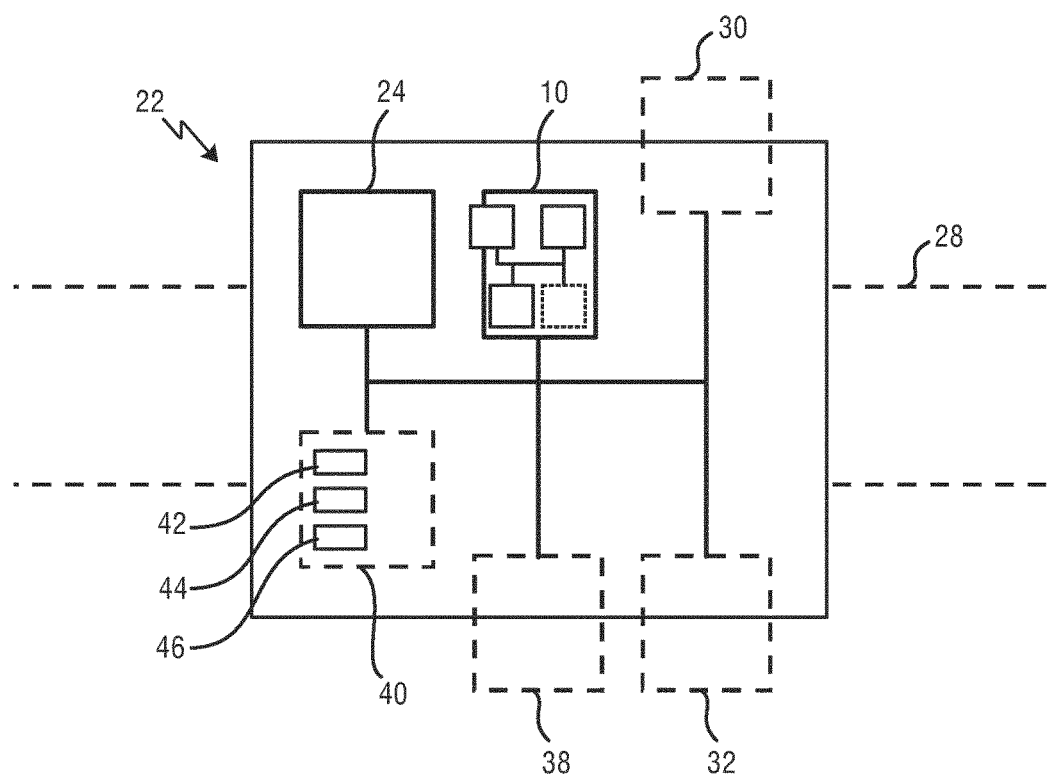
FIG. 5 schematically illustrates a wearable system according to an aspect of the present invention.

FIG. 5 schematically illustrates the system 22 in greater detail. Apart from the device 10, the system 22 includes the skin conductance sensor unit 24. Again, a dashed line indicates that a component may or may not be comprised in some embodiments. Optionally, the system 22 further includes an input user interface 30, which may particularly allow the user to provide information on his current sleep cycle, such as the time he gets up or the time he needs to get up in the near future. The system may further comprise an output user interface 32 by means of which the system 22 may provide information, e.g. the determined circadian phase shift, to the user. The input user interface and the output user interface may be implemented in the form of a touchscreen display or the like.

Additionally, the system 22 may further comprise a communication interface 38 for communicating with a circadian phase shift device. This communication interface may be implemented as a wired or wireless network interface such as a Bluetooth module, a ZigBee module or other wired or wireless communication module.

The required sleep cycle information for determining the external clock wake-up time may be acquired by means of a sleep cycle unit 40 that can also be included in the system 22. This sleep cycle unit 40 may include at least one of an acceleration sensor 42, a light sensor 44 and/or a temperature sensor 46. These different sensors may offer additional data indicating the time the user sleeps and the moment he gets up, i.e. the external clock wake-up time (in other embodiments the external wake up time may indicate the time the user should get up). For instance, the light sensor information may be taken as the prime source of information for the actual wake-up (time the user gets up or intends to get up, i.e. external clock wake-up time), possibly in conjunction with accelerometer data and skin temperature data. If the circadian clock of the user is out of sync with the local time, the minimum of the rise time of the skin conductance response, i.e. the internal clock wake-up time, will not be located at the same time the user actually gets up, i.e. the external clock wake-up time, but at an earlier or later time. In such cases a circadian phase mismatch may be repaired by means of circadian phase shifting.

Figure 6:
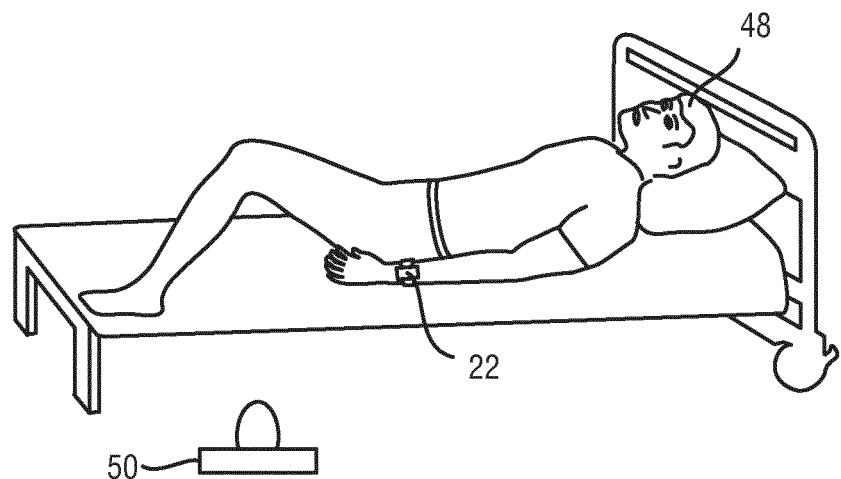
FIG. 6 illustrates the concept of controlling a circadian phase shift device by means of a system according to an aspect of the present invention.

FIG. 6 illustrates a possible application scenario of a system 22 according to the present invention. A user 48 wears a wristwatch-like system 22 which allows determining a circadian phase shift of the user 48. The system 22 may include a communication interface 38 in the form of a Bluetooth transceiver. The system 22 may further include a control unit 18 which allows determining control parameters for a circadian phase shift device 50. In this case, the system 22 might directly communicate with such a circadian phase shift device 50. As illustrated, a circadian phase shift device 50 may be represented by a wake-up light or a comparable device for providing a light stimulus. In other embodiments it may also be possible that the circadian phase shift device corresponds to a device a device for controlling an automated window shutter etc. Such a wristband may be worn 24/7 without inconvenience to the wearer. The real-time Bluetooth link allows other devices such as Wakeup light, or Golite blue, to respond the detected circadian phase, shifting it into the desired direction, if misaligned with the actual clock.

The circadian phase of a user is known to adapt to external stimuli, in particular light stimuli. Thus, such a device 50 for providing a light stimulus can be used for shifting the circadian phase of the user in a desired direction. When the circadian clock of a user is out of phase with the actual time, this is considered a health risk. Using the present invention in the form as illustrated in FIG. 6 for controlling a circadian phase shift device 50 may allow a user 48 to avoid this health risk.

In other embodiments it may also be possible that the circadian phase shift device corresponds to a device for providing an acoustic stimulus such as music.

Further embodiments of the present invention may also include implementations in which data, in particular a skin conductance signal, are recorded by means of an appropriate body-worn sensor device and the raw data are streamed to a device 10 according to an aspect of the present invention being implemented in the form of a smartphone app or Internet/network server.

Figure 7:
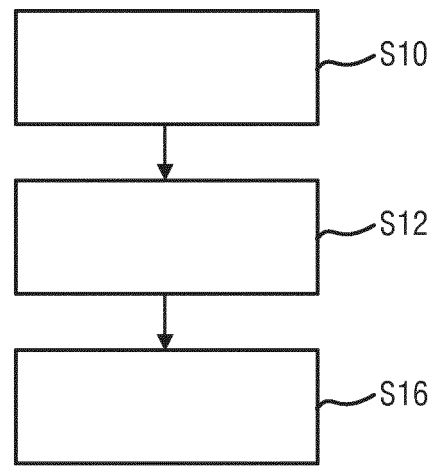
FIG. 7 schematically illustrates a method according to an aspect of the present invention.

In another aspect of the present invention as illustrated in FIG. 7, there is presented a method for detecting a circadian phase shift of a user. The method comprises the steps of obtaining (step S10) information of the user, determining (step S12) the internal and external clock wake-up times based upon the obtained information and evaluating (step S14) a circadian phase shift of the user based on the determined internal and external clock wake-up time. Such a method may be carried out by a processor in a personal computer, laptop, tablet, body-worn device, smartphone, Internet/network server, etc.

In general, the device, system and method of the present invention work best when the circadian clock (circadian phase shift) is shifted towards an earlier time compared to the outside world clock (external clock). The occurrence of a SCR rise time valley (i.e. a time period of decreased rise times of the skin conductance response) during sleep is not to be expected for healthy persons. Rather, one would expect a SCR rise time high, because of the nocturnal blood pressure dip. In a preferred embodiment of the present invention a circadian phase shift due to travel or other causes (stay in ICU, or periods of sedation, or prolonged stay underground) is estimated by comparing a normal daily rhythm of the SCR rise time valleys and hills to the present pattern. Then, in combination with information from other sensors a circadian phase shift (i.e. an estimation thereof) can be obtained.

It is known that the skin conductance of a user is related with the level of arousal of the user. Everything that emotionally touches the user activates the sweat glands in the skin, leading to a better conductor path through the skin. For example, in a lie detector or polygraph, a skin conductance sensor connected to the palm of the hand or the fingers is used. However, the skin conductance can also be measured on other parts of the body of the user. In WO2013/011416 (A1) a device for measuring the skin conductance of a user on the wrist of the user is disclosed. The present invention makes use of a comparable measurement approach to derive information on a circadian phase shift of a user.

A skin conductance response (SCR) may also be referred to as galvanic skin response (GSR), electrodermal response (EDR), psychogalvanic reflex (PGR) or skin conductance level (SCL). The SCR refers to method or, more precisely, the signal determined by means of a method of measuring the electrical conductance of the skin. This conductance varies depending on the amount of sweat-induced moisture on the skin. Sweat is controlled by the sympathetic nervous system. Consequently, skin conductance may be used as an indication of psychological or physiological arousal. If the sympathetic branch of the autonomic nervous system is highly aroused, then sweat gland activity also increases. This again results in an increased skin conductance. Thus, skin conductance can be used as a measure of emotional and sympathetic responses. As used herein the SCR is part of a skin conductance signal, i.e. the skin conductance signal describes the measure of the skin conductance over time and the SCR describes parts of this signal.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detecting a circadian phase shift of a user, comprising:
    an interface for obtaining a skin conductance signal of the user and sleep cycle information of the user;
    a processing circuit or determining an internal clock wake-up time based on the obtained skin conductance signal and an external clock wake-up time based on the obtained sleep cycle information; and
    wherein the processing circuit is configured to:
        determine a rise time of a skin conductance response based on the skin conductance signal; and
        determine a single time period of decreased average rise times of the skin conductance response by monitoring an average of the rise times of the skin conductance response, indicating the internal clock wake-up time;
    an evaluation circuit for evaluating a circadian phase shift of the user based on the internal clock wake-up time and the external clock wake-up time, and
    a control circuit for determining control parameters to control a circadian phase shift device based on the circadian phase shift of the user.

2. The device of claim 1, wherein the evaluation circuit is configured to compare the external clock wake-up time with the internal clock wake-up time to determine a time difference indicating the circadian phase shift.

3. The device of claim 1, wherein the sleep cycle information includes at least one of:
    acceleration sensor information indicative of a movement of a body part of the user;
    light sensor information indicative of an ambient light level in an ambience of the user; and
    skin temperature information indicative of a skin temperature of the user.

4. A wearable system for monitoring a circadian phase shift of a user comprising
    a device as claimed in claim 1; and
    a skin conductance sensor circuit for providing a skin conductance signal.

5. The system of claim 4, further comprising a wristband for supporting the system at a limb of the user.

6. The system of claim 4, wherein the skin conductance sensor circuit includes two electrodes for measuring a conductance when being applied to a skin portion of the user.

7. The system of claim 4, further comprising a sleep cycle circuit including at least one of
    an acceleration sensor for obtaining acceleration sensor information indicative of a movement of a body part of the user;
    a light sensor for obtaining light sensor information indicative of an ambient light level in an ambience of the user; and
    a temperature sensor for obtaining skin temperature information indicative of a skin temperature of the user.

8. The system of claim 4, further comprising an output user interface for providing information on the circadian phase shift of the user.

9. The system of claim 4, further comprising an input user interface for obtaining sleep cycle information from the user.

10. The system of claim 4, further comprising a communication interface for communicating with a circadian phase shift device.

* * * * *